US00PP16040P3

(12) United States Plant Patent
White

(10) Patent No.: US PP16,040 P3
(45) Date of Patent: Oct. 18, 2005

(54) MINIATURE ROSE PLANT NAMED 'SAVARED'

(50) Latin Name: ***Rosa hybrida* 'minima'**
Varietal Denomination: SAVared

(75) Inventor: Wendy R. White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 95 days.

(21) Appl. No.: 10/750,524

(22) Filed: Dec. 30, 2003

(65) Prior Publication Data

US 2005/0144691 P1 Jun. 30, 2005

(51) Int. Cl.[7] ..... A01H 5/00

(52) U.S. Cl. ..... Plt./122

(58) Field of Search ..... Plt./116, 122, 123, Plt./129

*Primary Examiner*—Howard J. Locker

(57) ABSTRACT

'SAVared' is a new and distinct variety of miniature rose plant primarily identified by the very strong fragrance in a red miniature rose. The plant is upright with medium to dark green, matte foliage. The attractive flowers may occasionally have exhibition rose form. They are held well above the plant, borne singly on long stems and in small sprays, and good as cut flowers.

1 Drawing Sheet

Genus/species: *Rosa hybrida* 'minima'.
Varietal denomination: 'SAVared'.
Commercial class: Miniature rose.

CROSS REFERENCE

This new invention relates to a new and distinct variety of hardy, dwarf, bush type rose plant, bearing some resemblance to 'BENfebu' (U.S. Plant patent application Ser. No. 10/318,843 with a filing date of Dec. 13, 2002). The flowers of both cultivars are a similar shade of red, with 23 to 28 petals, with those petals being about as long as they are wide. Both cultivars are of an upright growing habit, reaching up to 30 inches tall, with flowers primarily borne singly under similar growing conditions. The two primary differences between BENfebu and the new cultivar are that 'BENfebu' has more of its dark red flowers borne in clusters and that the reverse of these petals is flushed with white while on this new cultivar, the dark red flowers are borne more often singly and on longer stems and the reverse of its petals is the near the same shade of red as the top of the petals. Additionally, the anthocyanin coloration of the stems and foliage is mostly absent on BENfebu while it is always present and sometimes strong on the new cultivar.

The known relationship between these plants is that the miniature rose variety, 'Party Girl' (U.S. Plant Pat. No. 4,598) is in the parentage of both plants in the second generation back, and the miniature rose variety 'Baby Katie' (U.S. Plant Pat. No. 4,471) is in the third generation back for both plants.

BACKGROUND OF THE INVENTION

This present invention relates to a new and distinct variety of hardy, bush type plant of the miniature rose class. This new variety was created by me in a greenhouse in Rowley, Mass. by crossing the following two rose plants:

The seed parent is 'Taxi' (not under patent protection).

The pollen parent is an unintroduced seedling of ['Party Girl' (U.S. Plant Pat. No. 4,598) by 'SAVaspark' (U.S. Pat. No. 9,799)] by 'MACgenev', (U.S. Plant Pat. No. 8,279).

The main purpose of this breeding program is to produce unique miniature roses with hybrid tea form. We are also trying to reintroduce fragrance into roses along with disease resistance. Our ideal miniature rose would have fragrance and excellent disease resistance, along with hardiness and exhibition, hybrid tea form blooms in abundance from late spring to late fall.

To achieve this goal, various fragrant roses have been brought into the breeding program which, besides fragrance, were chosen for disease resistance and hardiness and then for hybrid tea, exhibition form. Those roses are mostly hybrid tea roses and with a couple of floribunda. These larger fragrant roses are then crossed with miniature roses, chosen for their disease resistance, durability and quality of bloom production in hopes of producing fragrant, hardy, disease resistant, floriferous miniature roses.

To create this rose, I used the very fragrant, hybrid tea rose, 'Taxi', noted for its good disease resistance and hardiness, as the seed parent. The pollen parent was a seedling that was the result of crossing a very floriferous miniature seedling from earlier in the hybridizing program, by the very fragrant hybrid tea, 'MACgenev'. This miniature seedling is, itself, fragrant and with tremendous bloom production and for those reasons was chosen for this particular cross.

This present invention, like its seed parent, 'Taxi', has red flowers with intense fragrance and with exhibition, hybrid tea form. Both plants have an upright growing habit. The most obvious difference between the two is that the seed parent is an hybrid tea rose while the new invention is a miniature rose. Although both roses are red, the new invention is a bluer-red while the seed parent is more of an orange-red.

The pollen parent is a fragrant, apricot miniature seedling. The similarities between this present invention and the pollen parent are the petal count and the fact that both are fragrant and miniature roses. This present invention is different from its pollen parent in plant habit and color. The new invention is red flowering and of upright habit. The pollen parent has medium-apricot colored flowers and a more spreading plant habit.

Asexual reproduction by cuttings of this new variety in Rowley, Mass., have shown root development to initiate in 1 to 2 weeks on cuttings taken from new growth, depending on light and temperature, and that these rooted cuttings, grown on, show all distinguishing characteristics to continually come true to form.

SUMMARY OF THE INVENTION

The present invention relates to a new and distinct variety of hardy dwarf bush type rose plant of the miniature class; the variety being primarily characterized—as to novelty—by it's intense fragrance in a red miniature rose with hybrid tea type form.

The variety is further characterized by:

Flowers borne mostly singly on long stems, ideal for cutting.

Repeat of bloom from late spring to early autumn.

Matte foliage.

Flowers held above the foliage on long stems, suitable for cutting.

A plant which grows and blooms both in the greenhouse and outdoors in the garden or in large containers providing decoration and fragrance.

BRIEF DESCRIPTION OF THE DRAWING

The accompanying color photograph taken in September shows specimens of the flower of this new variety in different stages of development as grown under plastic in Essex County, in Massachusetts.

BOTANICAL DESCRIPTION OF THE PLANT

Following is a detailed description in outline form pertaining specifically to this new and distinct variety of miniature rose plant as observed at 4 years of age, growing indoors, under plastic in 2 gallon containers, in Essex County, Massachusetts. All major color plate identifications made are referring to The Royal Horticulture Society Chart except where common terms of color definition are employed.

Genus/species: *Rosa hybrida* 'minima'.
Varietal denomination: 'SAVared'.
Commercial class: Miniature Rose.

FLOWERS

Blooming habit: Recurrent.
Borne: Mostly singly but also small clusters of 3 to 5.
Bud:
- *Size.*—Up to 13/16 inch in length and 9/16 inch diameter at the widest point just before the sepals divide.
- *Form.*—Ovate with an acuminate tip.
- *Color.*—When sepals first divide — near 60A.

Sepals:
- *Color.*—Outer surface, anthocyanin coloration present; general color is a medium, yellow-green, near 148C flushed with near 60C. Inside surface, a lighter yellow-green, near 138B and even lighter, near 138D at the center of each sepal.
- *Size.*—Inner two sepals are 1 1/8 inches long and 5/32 inch wide, outer three sepals are 1 1/4 inches long and 3/8 inch wide (excluding any foliar appendages).
- *Characteristics.*—Elongate with lanceolate tip, especially on the 3 outer sepals, occasionally teardrop with acuminate apex especially on the 2 inner sepals; fused at the receptacle; extending 1/2 inch beyond the tip of the bud just before the sepals start to divide; the 3 outermost sepals sometimes have 1 or 2 foliar appendages along one or both margins; rolling back to the stem where they remain until after the petals drop, being permanently attached to the receptacle.

Peduncle:
- *Length.*—Up to 1/4 inches.
- *Aspect.*—Straight, upright.
- *Strength.*—Strong.
- *Color.*—Medium yellow-green, near 146D, anthocyanin coloration present, flushing the peduncle with near 183A.
- *Texture.*—Glabrous.

Receptacle:
- *Diameter.*—5/16 inch.
- *Color.*—A medium yellow-green, near 144C.

Bloom:
- *Size.*—When fully expanded, averaging 2 inches across.
- *Form.*—High centered at first with a convex upper profile and the lower profile becoming flat; full open it has a flattened convex upper profile and an arched lower profile.
- *Petalage.*—Under normal conditions 23 to 28, most often having 24.
- *Fragrance.*—Strong.
- *Lasting quality as cut flower.*—5 to 9 days.
- *Petals.*—Texture: glabrous. Appearance: Inside — velvety, outside — satiny. Form: Broad spatulate. Base of petals: Oval. Length and width outer petals: 13/16 inch wide by 12/16 inch long. Arrangement: Arranged shingle like around receptacle. Persistence: Usually drop off cleanly in 7 to 10 days.
- *Color.*—During the first few days — Inner petals at the center of the flower: Upper surface is a cardinal red, between 53A and 53B; reverse is between 184B and 53B and a very light chartreuse green, near 1D, at the point of attachment. Outer petals — near 53B with near 59B feathering up and out from the center and base of the petals; reverse — near 187A, blending to near 59A at the margins and near 185C feathering from the center and base of petal and occasionally from a near white streak of near 159D going up the middle from the base of the petal and, at the point of attachment, a greenish-white, near 150D.

When half blown, the center petals are a currant red, between 46A and 46B; reverse is near 53B; outer petals are near 46B and the reverse is near 53B; and near 1D at the point of attachment.

As flower ages, the color lightens with both the inner and outer petals becoming near 68B with near 68A in the center and towards the base of each petal and near white, near 155D, at the base and point of attachment, just before the petals drop.

*General tonality.*—Cardinal red.

REPRODUCTIVE ORGANS

Stamens, filaments and anthers: Arrangement: (regularly arranged around styles). Quantity: 65 to 75.

*Filaments.*—Length — avg. 5/16 to 6/16 inch- inch. Color — a greenish white, near 157C, at the base and the upper ¾ becoming near 53A, a cardinal red.

*Anthers.*—Color — appearing dark red but near 185A from the greyed-purple group.

*Pollen.*—Color: A medium yellow-orange. Quantity: Small amount.

Pistils, styles and stigmas:

*Quantity.*—About half as many as the number of stamens.

*Styles.*—Thin and slightly undulate. Length: ¼ inch long. Color — near white at the base, near 8D at base, crimson upper ⅔, near 46A.

*Stigmas.*—Color — near 8D.

Hips: The plant produces hips and viable seeds, which are typical of the market class.

PLANT

Habit: Upright, well branched.

Growth: Average vigor, 18 to 30 inches tall and up to 20 inches in width.

Length of flowering stem: Often borne on the end of a lateral, 8 to 15 inches long when borne singly, except for the spring flush of bloom when singly borne flowers are usually on shorter stems, 6 to 10 inches or shorter, and there is a larger percentage of small sprays.

Foliage: Pinnately compound, usually 5 leaflets, with 3 leaflets right below the bud and occasionally 7 leaflets.

*Quantity.*—Abundant.

Size of mature leaf.—3⅞ to 5 inches from stem to tip when measured along the rachis.

Leaflets:

*Shape.*—Elongated ovate with an acute apex.

*Base.*—Usually oval, occasionally sides of leaflet are not attached to the petiole directly opposite each other at the base.

*Size mature terminal leaflet.*—Width 1 to 1¼ inches at its widest point length 1⅝ to 2 1/16 inches base to tip.

*Color.*—New foliage: Anthocyanin coloration present; upper surface, near 147A and flushed heavily with near 187A, under surface: Near 187D, if any green shows through, it is between 138B and 138A. Older foliage — anthocyanin coloring absent; upper surface: Between 147A and 139A, under surface near 147B.

*Appearance.*—Upper and lower surfaces matte; midveins protrude entirely while main lateral veins only protrude slightly.

*Texture.*—Upper surface is glabrous, under surface — leathery.

*Edge.*—Serration: Fine and uneven.

Petiole/rachis:

*Color on young leaf.*—Upper side: Near 187A from the greyed-purple group; underside: Flushed heavily with near 184B, also from the greyed-purple group.

*Color on old leaf.*—Upper side: Near 147A along edges and near 145C in the groove; underside: Near 137B along both sides and near 145C along the middle.

*Texture.*—Upper side: Coarse. Underside: Coarse with small thorns, prickles and hairs.

*Petiole/rachis.*—Length — 2¾ to 3 1/16 inches, on mature leaf.

Stipules: Margins are finely serrated with a nearly even serration on mature leaf measuring ⅞ inch in length.

Resistance: Average resistance to downy mildew, blackspot, and insects; good resistance to powdery mildew, no rust observed.

Wood:

*New wood.*—Color — between 146A and 147A, with a smooth texture.

*Old wood.*—Color — near 137B, with many thorns, prickles and hairs.

Thorns:

*Quantity on main stalks.*—As many as 14 to 16 per inch, random located and mixed in size.

*Size.*—3/32 inch to 11/32 inch in length and the length of the base of each thorn is as long as the thorn.

*On laterals.*—From where the lateral attaches to the main stem, quantity starts the same as on the main stem, although slightly smaller in size — from 3/32 inch to only 9/32 inch in length; progressing up the lateral, the quantity decreases, and from the bud down to the first leaf below the bud, there are no thorns or prickles.

*Form.*—A flat base, tapering to a point, and slightly curved downward.

*Color.*—When young: Near 182A, with tips of near 182C. When mature: From near 164A to 165A.

Winter hardiness: Tested hardy in zones 5 and 6, winter protection recommended for zones 7 and colder.

It is claimed:

1. A new and distinct variety of hardy miniature rose plant, substantially as illustrated and described, with strongly, fragrant flowers of a cardinal red, borne on an upright miniature rose bush with matte foliage.

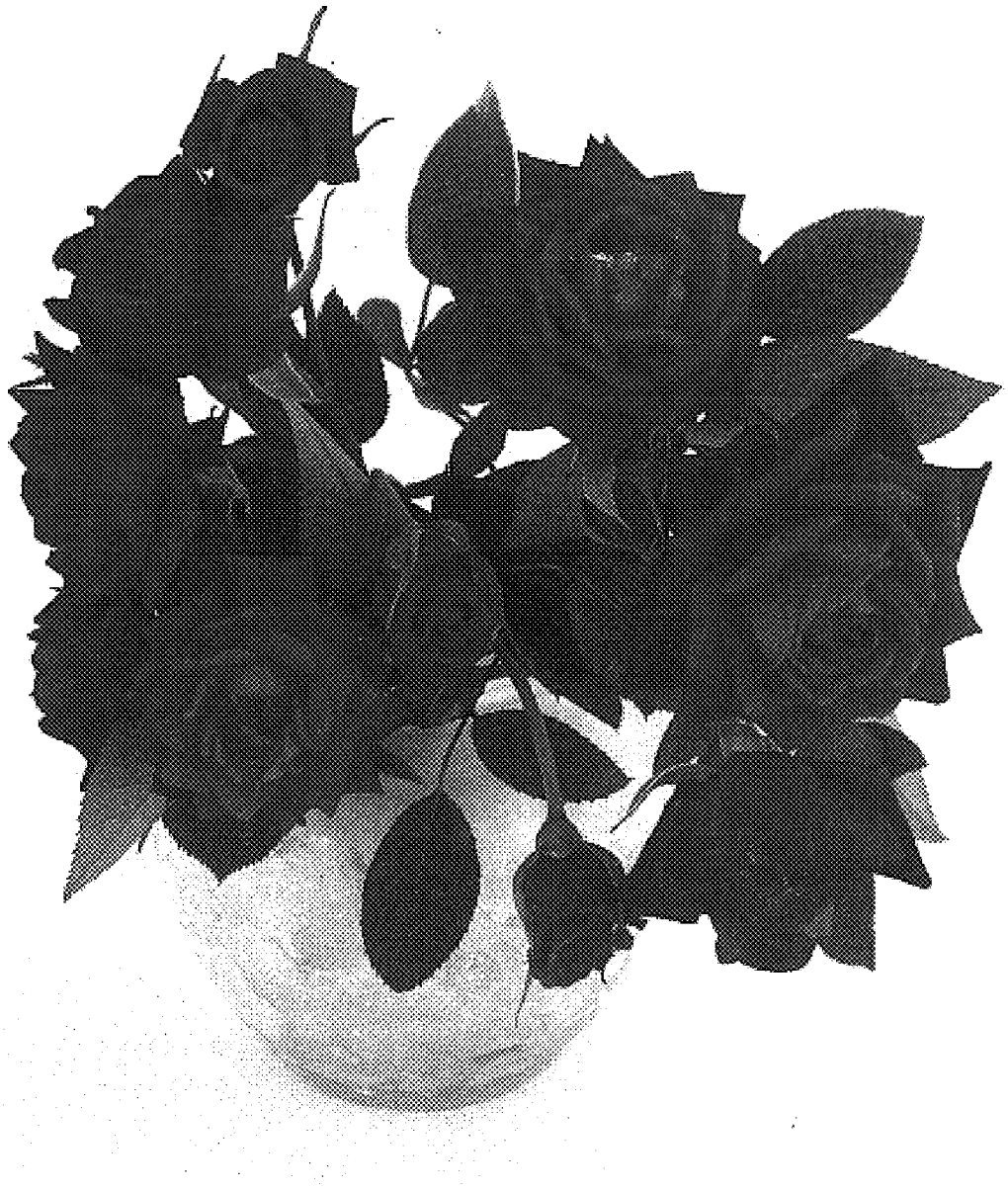

* * * * *